United States Patent [19]
Weber et al.

[11] Patent Number: 5,961,531
[45] Date of Patent: Oct. 5, 1999

[54] CONVERTIBLE RONGEUR

[75] Inventors: Helmut Weber; Gernot Weber, both of Emmingen-Liptingen, Germany

[73] Assignee: KMedic, Inc., Northvale, N.J.

[21] Appl. No.: 09/078,587

[22] Filed: May 13, 1998

[51] Int. Cl.⁶ .................................................. A61B 17/32

[52] U.S. Cl. ...................... 606/167; 606/168; 606/169; 606/170; 606/183; 604/22

[58] Field of Search .................................... 606/183, 184, 606/79, 83, 84, 167, 168, 169, 170; 604/22

[56] References Cited

U.S. PATENT DOCUMENTS

| | | | |
|---|---|---|---|
| 5,273,519 | 12/1993 | Koros et al. | 606/170 |
| 5,569,258 | 10/1996 | Gambale | 606/170 |
| 5,653,713 | 8/1997 | Michelson . | |
| 5,766,177 | 6/1998 | Lucas-Dean . | |

OTHER PUBLICATIONS

Tekno–Medical, Brochure/New Product Announcement, Nov. 1997, Germany.

*Primary Examiner*—Michael Buiz
*Assistant Examiner*—Len Ngo
*Attorney, Agent, or Firm*—Hughes Hubbard & Reed LLP; Ronald Abramson; Peter A. Sullivan

[57] ABSTRACT

A convertible rongeur is shown, with a top shaft that opens from the front, to allow access for cleaning, yet remains attached to the body of the device even when fully opened. In the preferred embodiment, the top shaft of the rongeur is held in positive engagement with the front handle piece of the rongeur by means of a spring loaded, retractable slot and pin linkage, and the permanent attachment between the top shaft and the remainder of the instrument is through a movable linkage at the rear. The rongeur is thus fully openable for cleaning, yet remains in one piece when opened for cleaning, and retains all of the advantages of permanently assembled prior art rongeurs.

7 Claims, 9 Drawing Sheets

CONVERTIBLE RONGEUR

BACKGROUND OF THE INVENTION

1. Field of the Invention

This invention generally relates to the field of surgical instruments, and more particularly to rongeurs for cutting and removing tissue, bone and the like during surgery.

2. Description of Related Art

Ronguers are used to excise tissue, degenerated disc materials or bone during surgical procedures. During regular use, tissue, blood, or other fluids collect in the voids between the top and bottom shafts of the instrument Multiple uses result in a buildup of material. To clean a rongeur thoroughly it must be disassembled.

Most rongeurs made today cannot easily be disassembled after surgery, and therefore cannot thoroughly be cleaned. The preferred method of cleaning surgical instruments is an ultrasonic cleaner. Ultrasonic cleaners cannot remove debris, e.g., blood, tissue or other buildups or deposits from inside the shaft, while the shaft is closed.

Figures 1A, 1B, 1C, 1D:
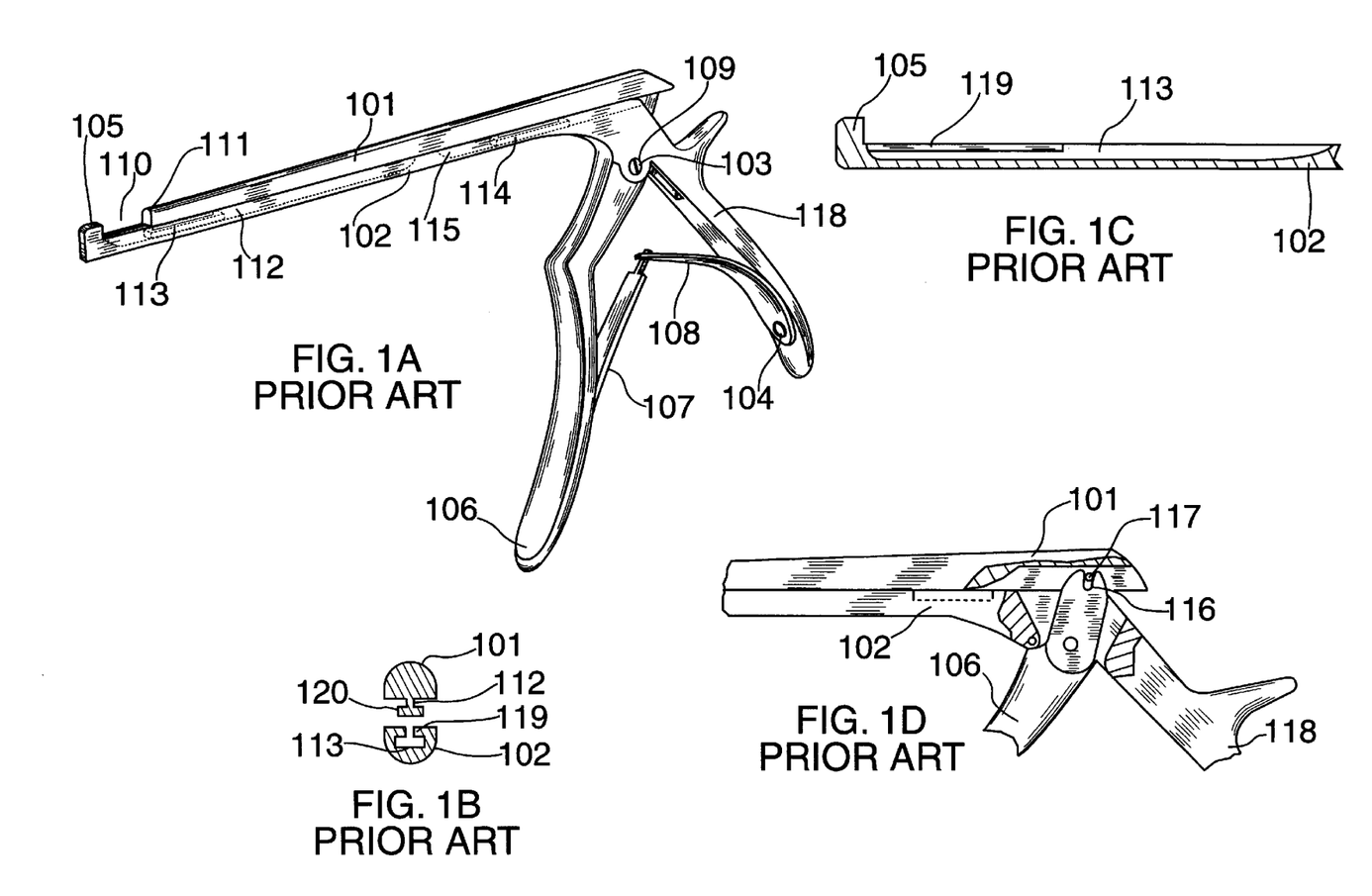
FIG. 1A shows a prior art rongeur.
FIGS. 1B, 1C and 1D shows, respectively, a section through an alignment guide on the top shaft of the prior art rongeur; a sectional elevational view of the interior channel in the bottom shaft of the prior art rongeur that receives an alignment guide, and the driving slot and driving pin mechanism employed to engage the front handle piece of the prior art rongeur with its top shaft.

A typical prior art rongeur is shown in FIGS. 1A–1D. Springs 107, 108 act to spread apart front handle piece 106 from the handle portion 118 of bottom shaft 102, pivoting about the shank of screw 103. Top shaft 101 is slidably positioned over bottom shaft 102 by means of alignment guides 112, 114 attached to top shaft 101 which fit into channels 113, 115 in bottom shaft 102 and are held in place by channel constrictions, one of which (119) is shown. Top shaft 101 is slidably driven forward and backward by the pivoting movement of front handle piece 106, the driving slot (116) of which engages driving pin 117 in top shaft 101 to supply the driving force thereto.

When handles 106, 118 are not being squeezed, the action of springs 107 and 108 results in top shaft 101 being fully retracted toward the rear of the instrument. The gap 110 in front of top shaft 101 in this position is called the "bite opening." The front 111 of top shaft 101 and "foot plate" 105 against which it touches when handles 106, 118 are fully compressed, are cutting surfaces. When these cutting surfaces contact, they "bite," and thus remove material held in the bite opening. Rongeurs are available in a variety of foot plate profiles and bite opening dimensions, as well as in different sizes and configurations of the handles and shafts. Typically, a range of different rongeurs will be available to a surgeon for use during a surgical procedure.

Most prior art rongeurs require tools to disassemble and are difficult to reassemble. The following are the steps necessary to disassemble a typical prior art rongeur such as the one shown in FIGS. 1A–1D.

Most prior art rongeurs require tools to disassemble and are difficult to reassemble. The following are the steps necessary to disassemble a typical prior art rongeur such as the one shown in FIGS. 1A–1D.

- Loosen screws (104 etc.) holding springs 107, 108 (stripping is likely, ruins the screws)
- Loosen and remove screw 103
- Pull front handle piece 106 down, disengaging driving slot 116 from driving pin 117
- Slide top shaft 101 back, disengage alignment guides 112, 114 from channels 113,115, and remove, The following are the steps necessary to reassemble such a prior art rongeur.

- Select matching parts for the rongeur being reassembled
- Reseat alignment guides 112, 114 protruding from top shaft 101 in channels 113, 115 in bottom shaft 102
- Align top shaft 101 so that driving pin 117 is opposite position where driving slot 116 will reinsert (easy to mistake correct position)
- Insert screw 103 and tighten
- Align springs 107, 108 together (and tighten screw 104 and opposing screw (not shown), if necessary), Note that in reassembly, there is no positive indication of proper position. In addition, the slot of screw 103, and possibly other screws, will burr with repeated removal, resulting in holes in gloves and injury.

In summary, the problems encountered with disassembling prior art rongeurs include the following:

1. Tools are required, screws must be taken out which are not meant to be removed. It is very easy to strip a screw or cause burrs on the screw head. This can lead to a dangerous situation in the operating room if a surgeon's glove is torn by burrs on the screw head.
2. When rongeurs are disassembled the instrument is in a number of parts (e.g., 101, 102, 106, 107, 108, 109, etc.), which can be easily lost or misplaced during the cleaning process.
3. Rongeurs are used in sets with varying sizes of tips and shaft lengths. Parts from different rongeurs can be confused, resulting in an improperly reassembled instrument that malfunctions, binds or comes apart.
4. Putting rongeurs back together requires training. A rongeur that is not properly reassembled may fail in the operating room causing possible injury to the patient, valuable time loss during the procedure, and damage to the instrument.

Due to these problems, a need was perceived to devise a new rongeur that would overcome the problems noted above, but without compromising any of the utility of prior art rongeurs.

BRIEF SUMMARY OF THE INVENTION

It is an object of the present invention to provide a openable rongeur that readily permits thorough interior cleaning, yet remains as one unit with no loose parts when opened for cleaning.

Further objects of the invention include the following:

An instrument that can be opened, allowing an ultrasonic cleaner to clean the entire instrument effectively.

An instrument that stays together in one piece, thereby avoiding loose parts that can be lost.

An instrument that, after being opened and cleaned, can be reassembled by a novice without the use of tools.

An instrument that, after reassembly, reliably functions as intended.

An openable yet unitary instrument that has no functional disadvantage as compared to prior art rongeur designs.

The objects of the invention are achieved through a convertible rongeur with a top shaft that opens from the front, to allow access for cleaning, yet remains attached to the body of the device even when fully opened. In the preferred embodiment, the top shaft of the rongeur is held in positive engagement with the front handle piece of the rongeur by means of a spring loaded, retractable slot and pin linkage, and the permanent attachment between the top shaft and the remainder of the instrument is through a movable linkage at the rear.

The rongeur of the present invention has a mechanism that remains in one piece when opened for cleaning, unlike any rongeur known in the prior art, yet retains all of the advantages of permanently assembled prior art rongeurs.

The manner in which said objectives are attained are further shown by the drawings enumerated below, and the accompanying detailed description It should be apparent therefrom that although the invention has been illustrated with a preferred embodiment involving a retractable front handle piece, its principles could equally well be implemented in other ways without departing from the scope and spirit of the invention.

DETAILED DESCRIPTION OF THE INVENTION

Figure 2:
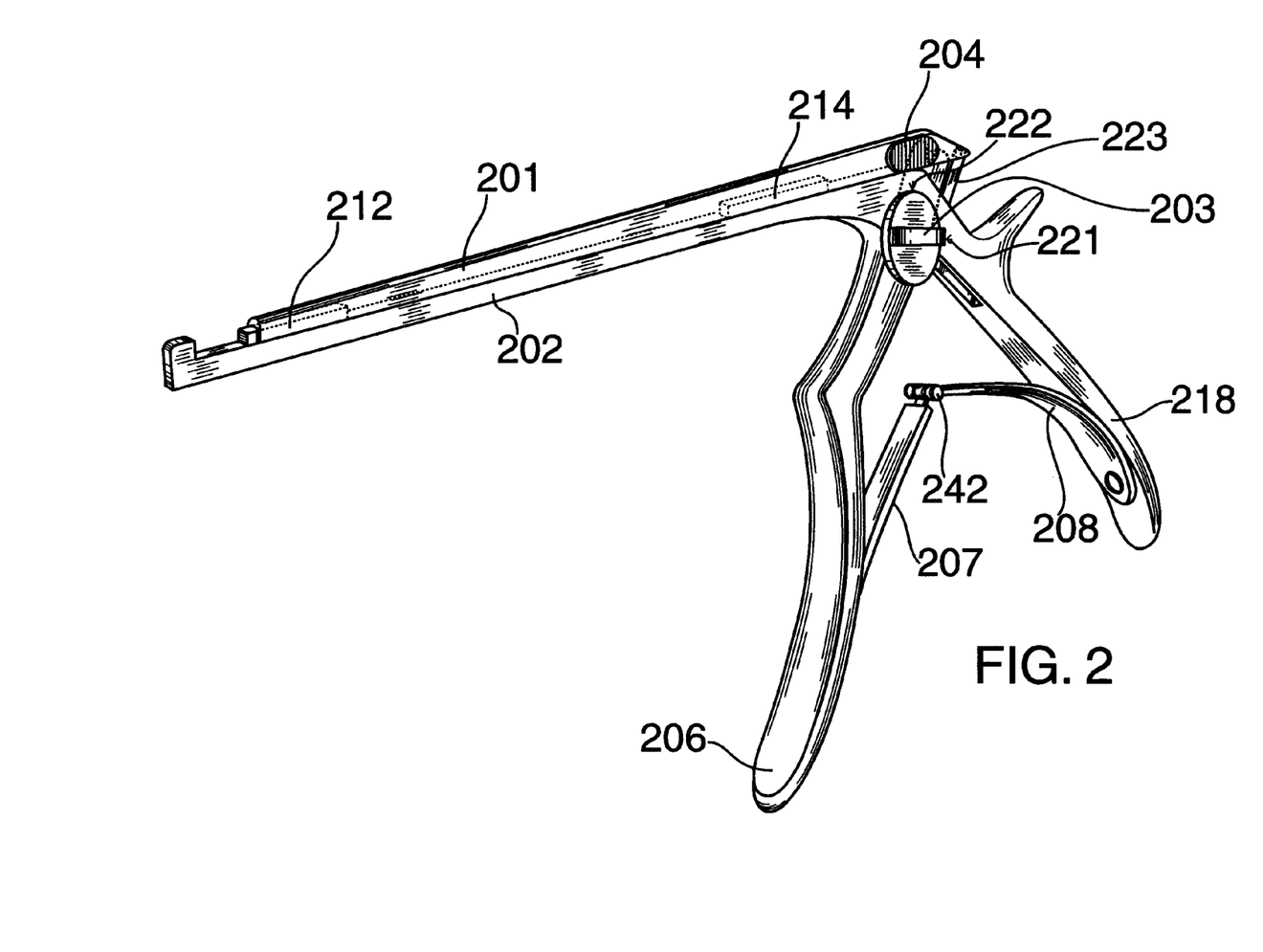
FIG. 2 is a perspective view of the preferred embodiment with the release knob in the closed position.
Figure 3:
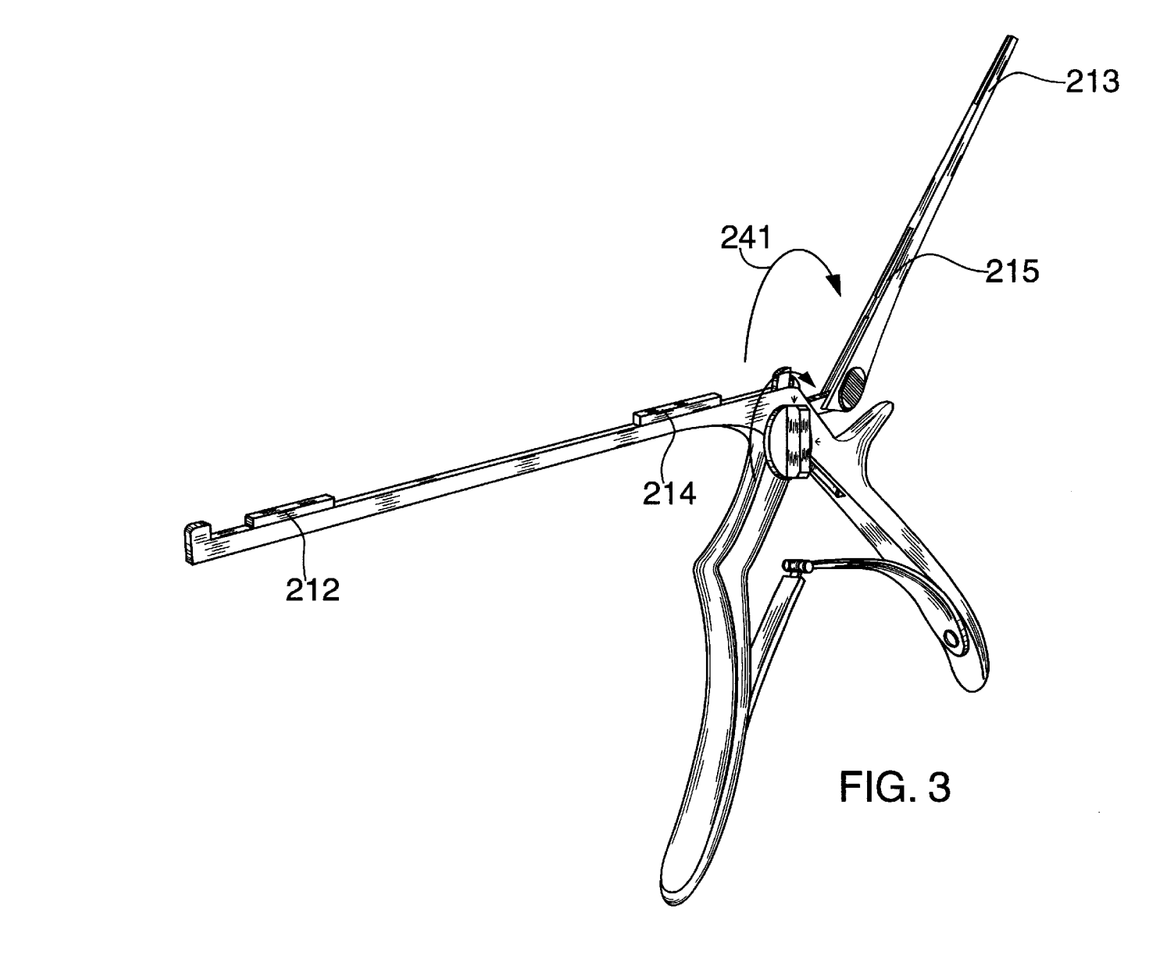
FIG. 3 is a perspective view of the preferred embodiment with the release knob in the open position and the top shaft opened.
Figure 4A:
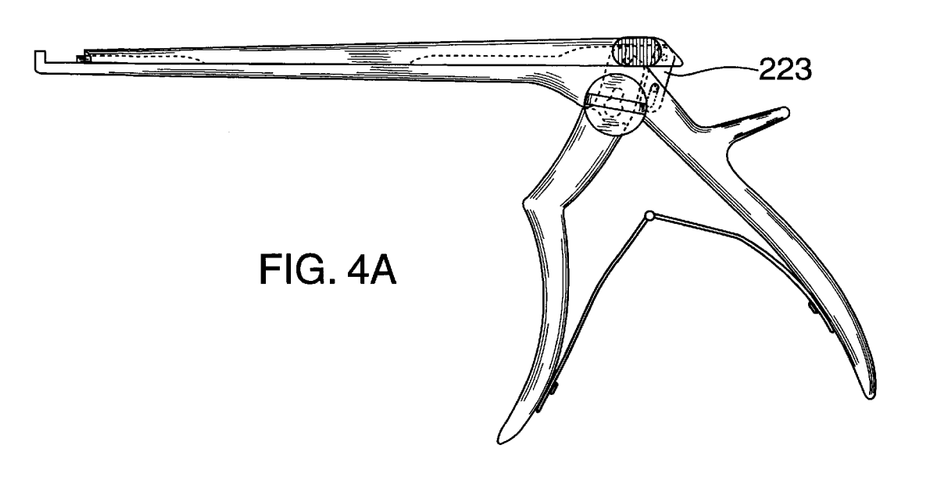
FIGS. 4A and 4B are, respectively, a side elevational view of the preferred embodiment with the top shaft retracted, and with the handle compressed to move the top shaft forward.
Figure 4B:
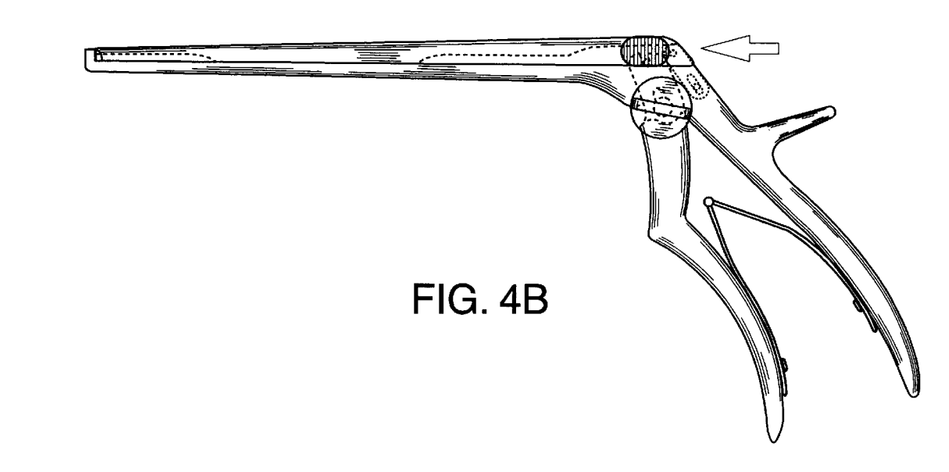
Figure 4C:
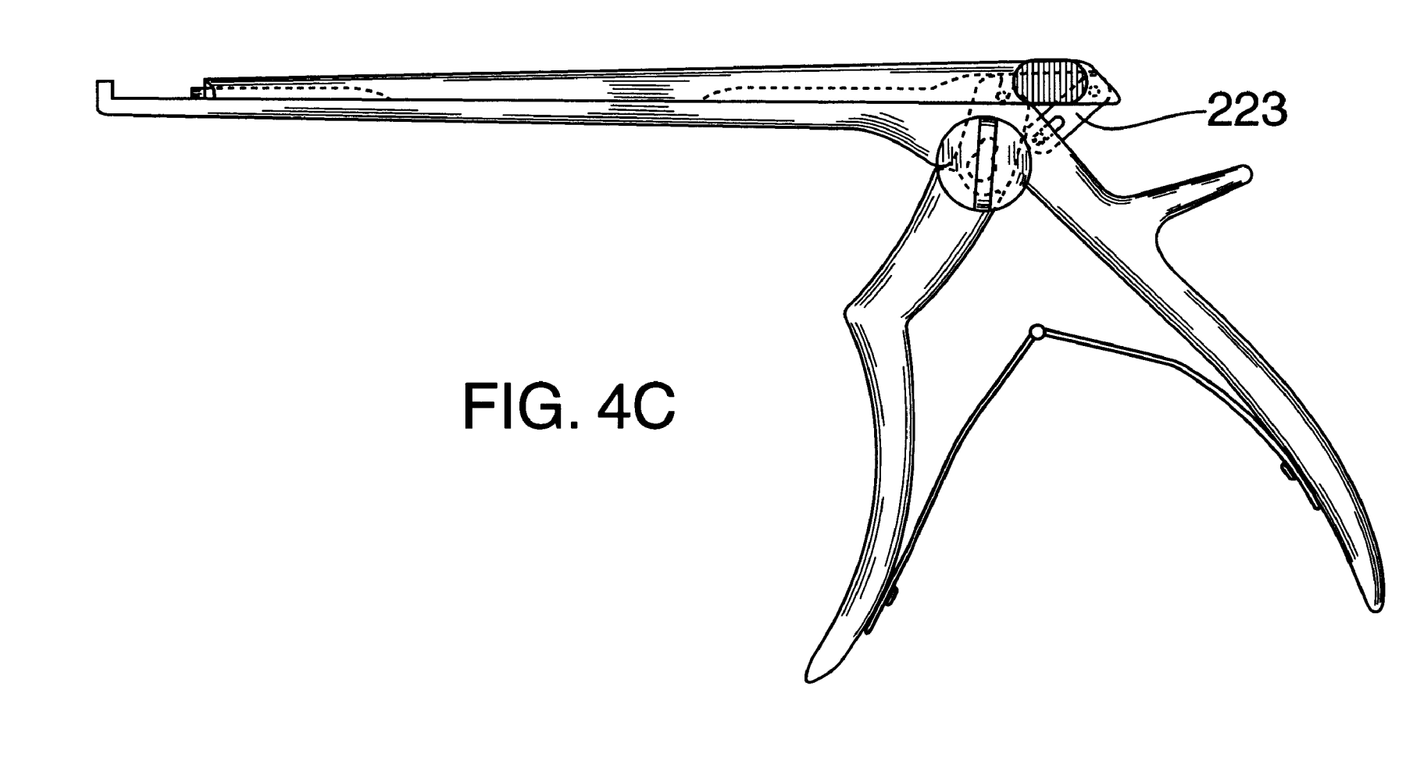
FIG. 4C is a side elevational view with the release knob rotated to disengage the top shaft to allow it to be opened for cleaning.
Figure 4D:
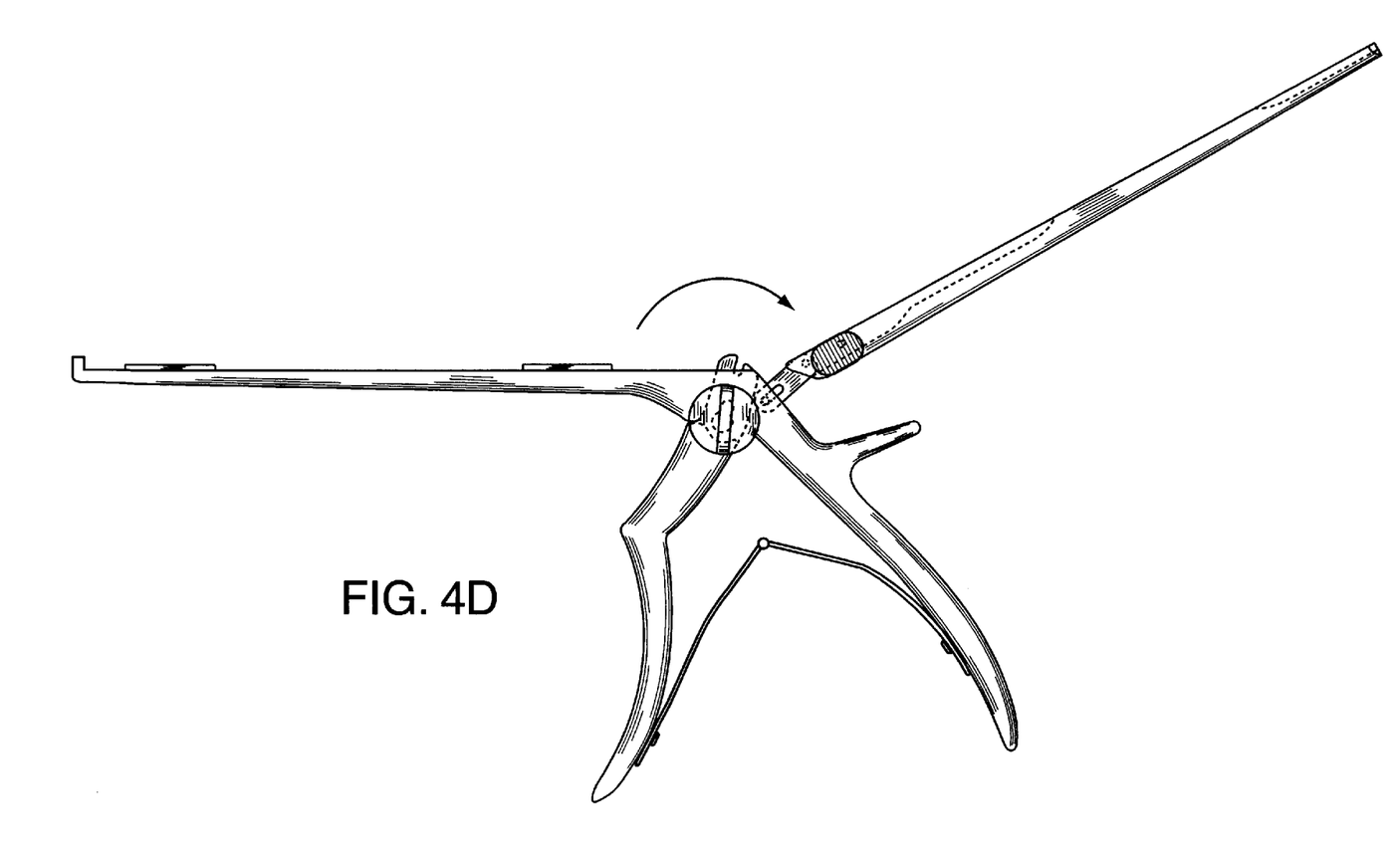
FIG. 4D is a side elevational view with the top shaft opened for cleaning.
Figure 5A:
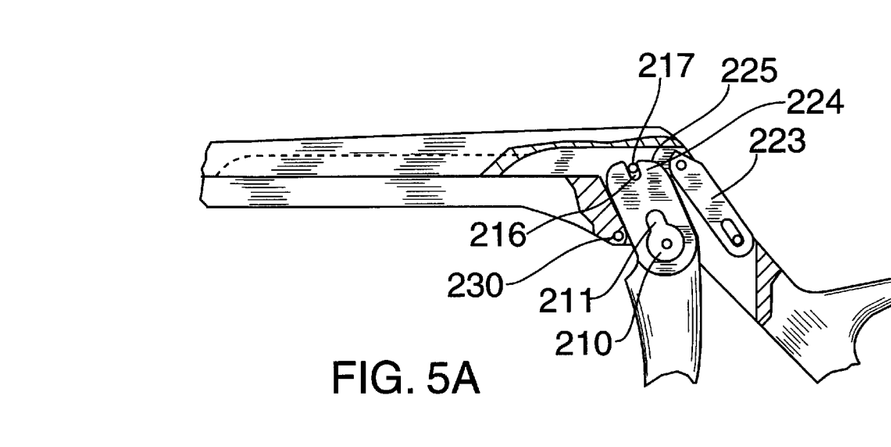
FIGS. 5A, 5B and 5C are, respectively, side elevational views, partially sectional, without knob, to show linkage operation from closed (5A) to opening (5B) to open (5C).
Figure 5B:
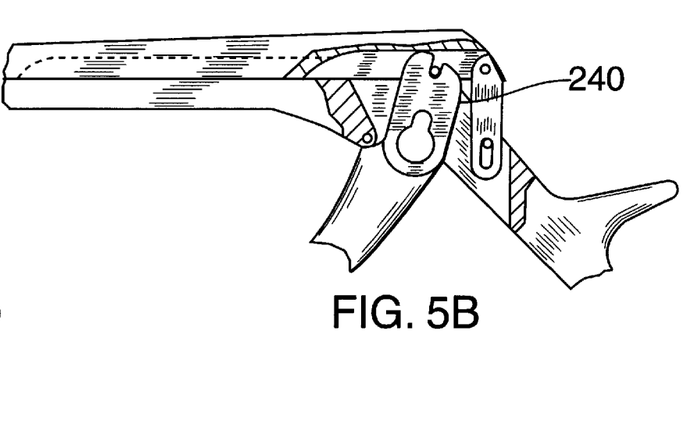
Figure 5C:
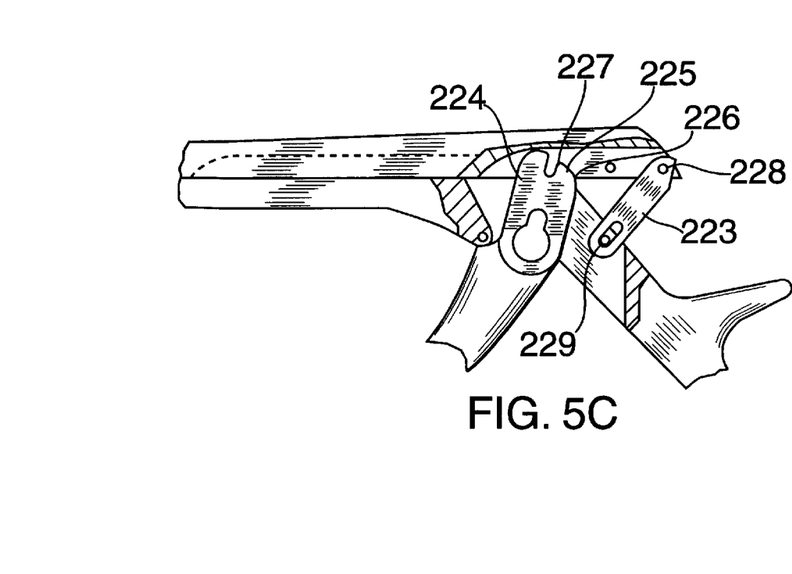
Figure 6A:
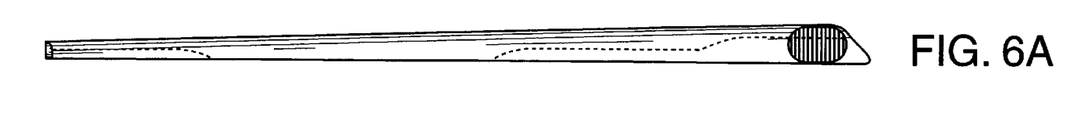
FIGS. 6A–6F are side elevational views of the major components of the preferred embodiment separated from one another.
Figures 6B, 6C, 6D, 6E, 6F:
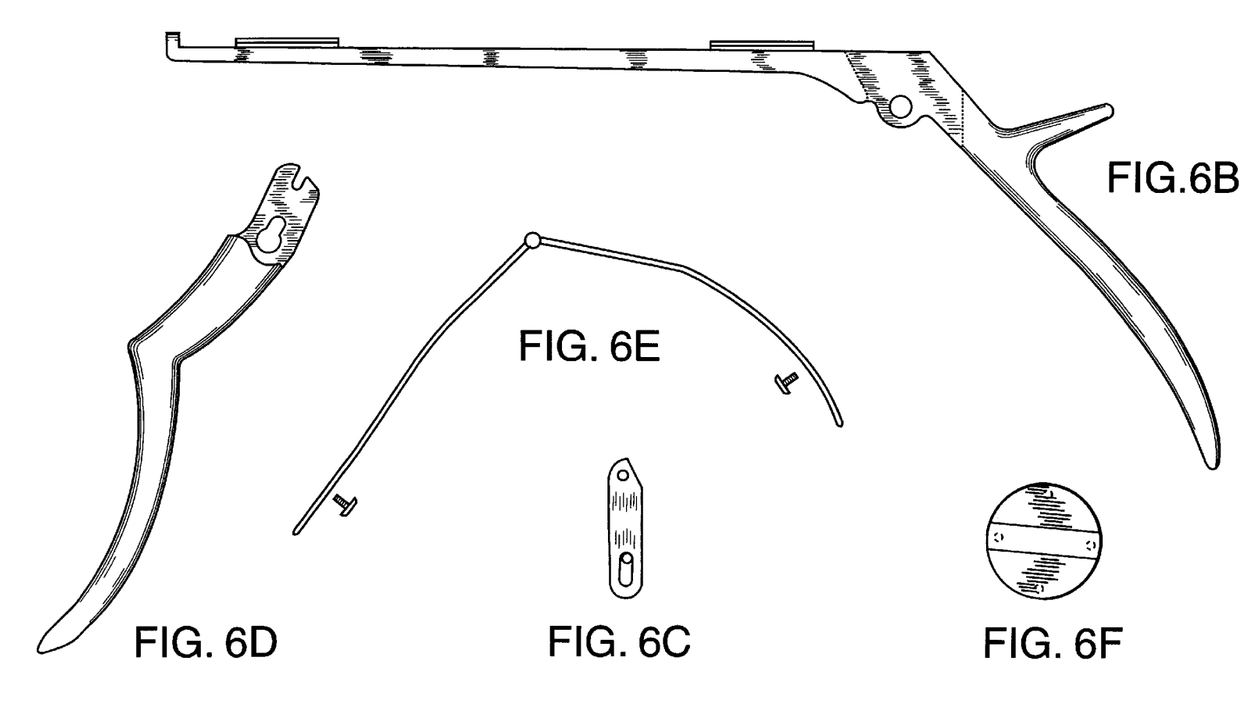
Figure 7A:
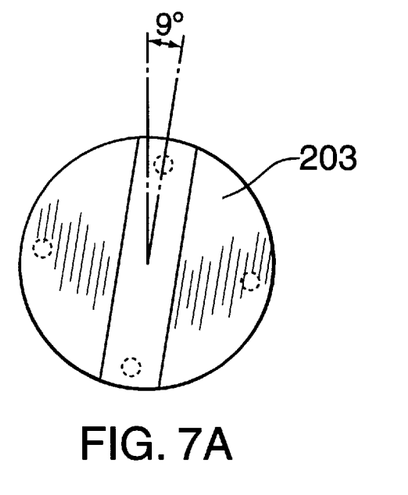
FIG. 7A shows a top plan view of the release knob, showing a 9° from vertical alignment in the open position.
Figure 7B:
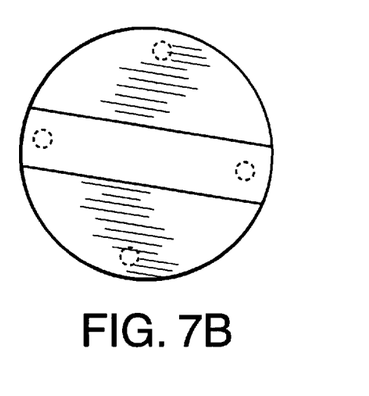
FIG. 7B shows the release knob in the closed position.
Figure 8A:
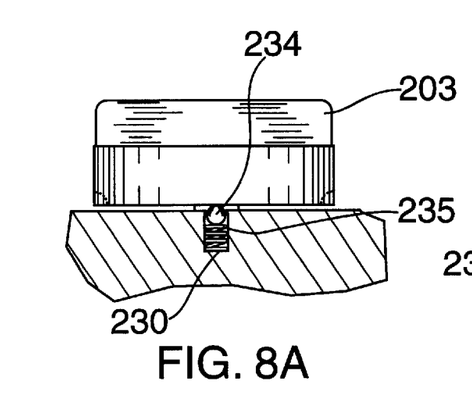
FIGS. 8A and 8B show side elevations, partially sectional, of the release knob, with ball bearing/spring assembly respectively retracted and biased upward into concave depression on the knob.
Figure 8B:
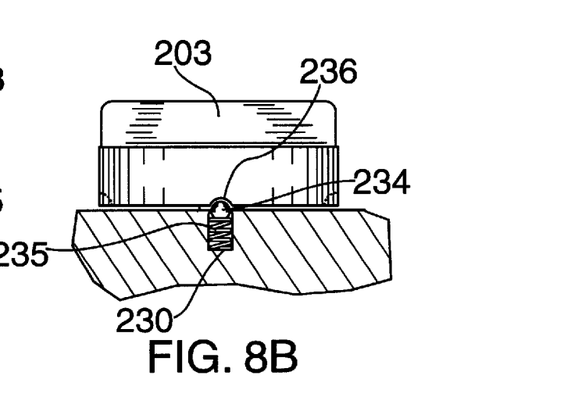
Figure 9A:
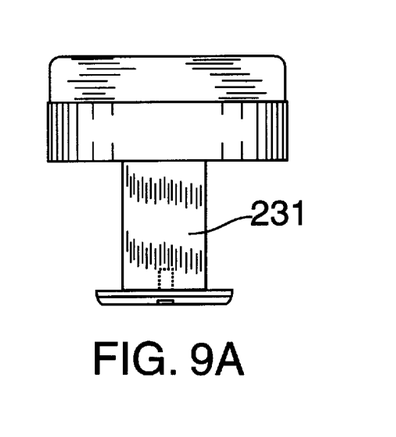
FIGS. 9A and 9B show side sectional views of the release knob, center shank and screw in closed and open positions, respectively.
Figure 9B:
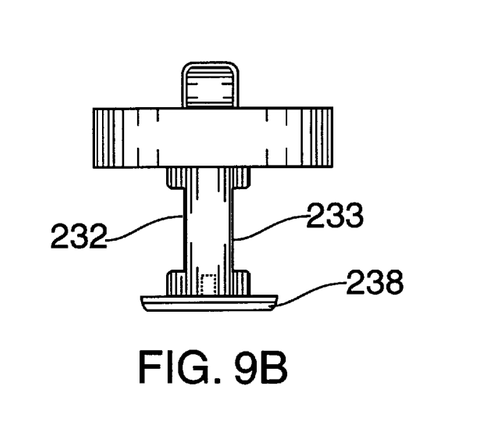

The preferred embodiment of the invention is illustrated in FIGS. 2–9B, as well as in FIGS. 10A–16B, and described in the text that follows. The reader should bear in mind, however, that what follows is a description of a particular embodiment, and that the details of this embodiment are not intended to limit the scope of the invention.

Release knob 203 has closed and open positions 221, 222 with stops indicated by spring-loaded ball bearing-detent mechanism 234, 235, 236. In the open position, center shank's (231) two flat surfaces 232, 233 line up with narrow part 211 of keyhole 210, allowing driving slot 216 in front handle piece 206 to be retracted from engagement with driving pin 217 in upper shaft 201. When aligned in the open position, narrow surfaces 232, 233 of center shank 231 (FIG. 9B) are presented to the narrow length 211 of keyhole 210, and accordingly center shank 231 is freed so that it may be moved up and down relative to said narrow length 211 of keyhole 210. When driving pin 217 in upper shaft 201 is engaged with driving slot 216 in front handle piece 206, and release knob 203 is in the closed position (wherein center shank 231 presents its wide aspect (FIG. 9A) to the narrow portion 211 of keyhole 210, and thus said center shank 231 is fixed in the lower part of keyhole 210), the instrument functions normally.

Springs 207, 208 hold open front handle piece 206 and the handle portion 218 of bottom shaft 202, biasing the round bottom surface of keyhole 210 in front handle piece end 224 upward, against the round lower surface of center shank 231. When center shank 231 is in the closed position, presenting its wide aspect (FIG. 9A) against the narrow upper portion 211 of keyhole 210, the front handle piece 206 is locked in place. When center shank 231 is rotated to the open position, its narrow sides 232, 233 (FIG. 9B) are presented to the narrow portion 211 of the keyhole 210, allowing said narrow portion 211 to slide over said narrow center shank sides 232, 233, thereby allowing the front handle piece 206 to be moved downwardly against the spring bias relative to the center shank 231. Pulling back on pinch grip 204 in this situation pushes driving pin 217 against the backside 227 of driving slot 216 so as to push front handle piece end 224 downward and out of the way, allowing top shaft 201 to be pulled back so that its alignment guides 212, 214 disengage from channels 213, 215 in the top shaft 201. Continued backward pressure on pinch grip 204 results in top shaft 201 flipping up and back into the fully open position as shown (241), held to the rear of bottom shaft 202 by elongated link 223.

During reassembly, top shaft 201 is lowered so that channels 213, 215 slip over alignment guides 212, 214. The top shaft 201 is then pushed forward, engaging the side ribs of the alignment guides 212, 214 in the horizontal constrictions toward the rear of channels 213, 215. When top shaft 201 is thus pushed forward, driving pin 217 moves forward along bottom shaft 202, strikes radius 226, and ramp 225, again to push front handle piece end 224 downward and out of the way, allowing driving pin 217 to seat in driving slot 216 as top shaft 201 clicks into place. Springs 207, 208 bias the driving slot 216 against the driving pin 217 to hold the mechanism in place, while release knob 203 is rotated into the closed position to lock in place front handle piece 206 as engaged with top shaft 201. Assembly is then complete, and the instrument is ready for use.

Driving slot 216 is not symmetrical. Due to a 14° slant from vertical (FIG. 11A), it has an early exit on backside 227 with radius 226 and ramp 225 for driving pin 217 to travel along. (The profiles of backside 227, radius 226 and ramp 225, and the respective 9° and 14° slant angles of release knob 203 and driving slot 216, are observed to work in the preferred embodiment to make the release mechanism operate smoothly, but neither these profiles nor slant angles are believed to be critical to the fabrication of a working convertible instrument.) The position of ramp/radius 225, 226 relative to horizontal shaft/base 202 facilitates the "snap in" operation of the preferred embodiment. As noted above, driving pin 217 does not move vertically during seating and unseating; the front handle piece 206 with driving slot 216 actually moves down and out of the way as driving pin 217 is slid forward.

The screw 238 backing up release knob 203 is permanently locked into place. BaHl bearing 234 and spring 235 in detent mechanism 234, 235, 236 is permanently installed in drill hole 230. Disassembly of any parts requiring tools is to be done by the manufacturer only.

Once the instrument is opened, thorough cleaning with an ultrasound cleaner can be performed. Elongated link 223 holds pieces 201 and 206 together with link pins 228 and 229 and a corresponding hole and slot, and does not interfere with the function of instrument. The instrument remains in one piece throughout the cleaning cycle.

Release knob 203 is "idiot-proof" can be turned either to the left or right in order to open or close the apparatus.

Pinch grip 204 on end of top shaft 201 provides easy pullback, and etched legend (not shown) on the top shaft 201 denote correct place and direction in which to apply force.

Handle springs 207, 208 are precisely set. Their mountings are under spring pressure. Constant upward spring pressure ensures that driving pin 217 will remain seated within driving slot 216 when not locked in place by the effect of the circular portion of shank 231 contacting against the bottom round portion of keyhole 210. The constant spring pressure also holds open the handle pieces 206, 218, thereby retracting top shaft 201 to its fully open position in the resting state of the instrument. Unlike a typical prior art rongeur as shown in FIG. 1 (in which the springs 107, 108, are merely removeably interlocked with a fork and tine structure), the convertible rongeur as implemented in the preferred embodiment uses a closed hinge structure 242 to attach spring 207 to spring 208, in order to ensure continued upward pressure from the springs when release knob 203 is in the open position and/or front handle piece 206 is retracted.

The apparatus described above, comprising a convertible rongeur which remains in one unitary structure even when fully opened for cleaning, has been illustrated with a particular preferred embodiment in which a driving pin slides over a ramp to seat in a driving slot in the front handle piece which has been retractably secured to the bottom shaft of the rongeur. However, the means for engaging the front handle piece of the rongeur with the top shaft thereof, shown in the preferred embodiment as a slot and pin mechanism, could be any other means of engagement, such as a tongue in groove, a cog or gear linkage, a friction linkage, a magnetic linkage, or any other means or positive attachment. The means for disengaging said engagement means, shown in the preferred embodiment as a sliding engagement into a retractable slot piece, could be by any other means for disengaging the chosen means of engagement, such as by releasing the back edge 240 of front handle piece 206 so as to swing rear and clear of driving pin 217 (or alternate engagement part), or a lever or other means for retracting front handle piece 206 so as to disengage the engagement means components. The attachment means, illustrated in the preferred embodiment with elongated link 223, could be comprised as well of a loop of wire or other material, a strap, a tape, a lever, or any other means of attachment of any size or shape. The closed hinge structure 242, illustrated in the preferred embodiment as a fully enclosed hinge structure, could be any form of rotatable or hinged attachment that does not readily detach when front handle piece 206 is loosened or retracted during disassembly or assembly.

It is apparent from the foregoing that a new convertible rongeur has been developed that accomplishes the stated objects of the invention. While the presently existing embodiment has been described in detail, it will be apparent to those skilled in the art that the principles of the invention are readily adaptable to other adaptations and configurations of the apparatus described herein without departing from the scope and spirit of the invention, as defined in the following claims.

I claim:

1. A convertible rongeur comprising a front handle piece pivotably attached to a pivot point in a bottom shaft piece having a tip portion and a handle portion, engagement means whereby said front handle piece is engaged with a top shaft cutting piece so as to slideably advance and retract said top shaft cutting piece relative to the tip portion of said bottom shaft piece when said front handle piece is compressed relative to said handle portion of said bottom shaft piece, spring means to resist said compression and hold said front handle piece apart from said handle portion of said bottom shaft piece, wherein release means permits said top shaft cutting piece to open from the front, to allow access for cleaning, and wherein said top shaft cutting piece, when so opened, remains attached by attachment means to the body of the rongeur, so as to retain all parts of said rongeur in one attached unit at all times.

2. A rongeur as in claim 1, wherein said engagement means comprises a driving slot in the top end of said front handle piece that engages a driving pin in said top shaft.

3. A rongeur as in claim 2, wherein said release means comprises a retractable mounting for said front handle piece, which when biased so as to retract said front handle piece, permits said driving pin to unseat from said driving slot and slide over said top end of said front handle piece.

4. A rongeur as in claim 3, wherein said front handle can also be retracted so that said driving pin may slide back over said top end of said front handle piece so as to reseat in said driving slot.

5. A rongeur as in claim 1, wherein said attachment means comprises a metal link pivotally attached at one end thereof to the rear porion of said top shaft cutting piece "and a central point on the top side" to of said bottom shaft piece.

6. A rongeur as in claims 3 or 4, wherein said driving slot is positioned so as to slant rearward at an angle of approximately 14 degrees from the vertical, and wherein said front handle piece comprises a radius and a ramp to the rear of said slot so as to facilitate the sliding of said driving pin over said top end of said front handle piece.

7. A rongeur as in claim 3, wherein said spring means comprise two elongated spring pieces each having a top and bottom end, the bottom ends of which are attached, respectively, to said front handle piece and said handle portion of said bottom shaft piece, and the top ends of which are rotatably or hingably joined together in a manner such that said springs do not readily detach from each other when said front handle piece is loosened or retracted.

\* \* \* \* \*